(12) United States Patent
Jenkins

(10) Patent No.: US 10,485,283 B2
(45) Date of Patent: Nov. 26, 2019

(54) SAFETY GLASSES DEPLOYMENT SYSTEM

(71) Applicant: Worldwide Vision Technologies, LLC, Oak Ridge, NJ (US)

(72) Inventor: Brian Dennis Jenkins, Oak Ridge, NJ (US)

(73) Assignee: Brian Dennis Jenkins, Oak Ridge, NJ (US)

( * ) Notice: Subject to any disclaimer, the term of this patent is extended or adjusted under 35 U.S.C. 154(b) by 1019 days.

(21) Appl. No.: 14/845,819

(22) Filed: Sep. 4, 2015

(65) Prior Publication Data

US 2017/0065019 A1    Mar. 9, 2017

(51) Int. Cl.
*G02C 5/12* (2006.01)
*A42B 3/18* (2006.01)
*A61F 9/02* (2006.01)
*G02C 3/00* (2006.01)
*G02C 3/02* (2006.01)

(52) U.S. Cl.
CPC .............. *A42B 3/185* (2013.01); *A61F 9/025* (2013.01); *A61F 9/026* (2013.01); *G02C 3/003* (2013.01); *G02C 3/006* (2013.01); *G02C 3/02* (2013.01); *G02C 5/12* (2013.01)

(58) Field of Classification Search
CPC .......... G02C 5/126; G02C 5/12; G02C 5/122; G02C 3/003; G02C 1/04; G02C 3/00; G02C 3/006; G02C 3/02; G02C 5/00; G02C 5/02; G02C 5/10; G02C 5/124; G02C 5/143; G02C 7/10; G02C 9/04; G02C 11/08; A61F 9/025; A61F 9/026; A61F 9/06; A42B 3/14; A42B 3/185

USPC ......... 351/44, 47, 57, 78–88, 106, 121–128, 351/130–139, 155–158, 178
See application file for complete search history.

(56) References Cited

U.S. PATENT DOCUMENTS

| | | |
|---|---|---|
| 4,045,137 A | 8/1977 | Bradley, Jr. |
| 4,102,566 A | 7/1978 | Shelton |
| 4,723,844 A | 2/1988 | Medina |
| 4,787,729 A | 11/1988 | Ruffen |
| 4,818,092 A | 4/1989 | Bononi |
| 4,953,967 A | 9/1990 | Somerville |
| 5,200,771 A | 4/1993 | Schmolz et al. |
| 5,467,148 A | 11/1995 | Conway |
| 5,526,070 A | 6/1996 | Simioni |
| 5,583,586 A | 12/1996 | Evans |
| 5,771,087 A | 6/1998 | Martin et al. |

(Continued)

*Primary Examiner* — Mustak Choudhury
(74) *Attorney, Agent, or Firm* — Lerner, David, Littenberg, Krumholz & Mentlik, LLP

(57) ABSTRACT

An eyewear system having a lens and a nasion pad is disclosed. The nasion pad is configured to fit on a user's nasion and at least partially secure the eyewear in position. In one embodiment, the nasion pad has a saddle shape to prevent movement or rotation of the eyewear with respect to the user's face. A nose contact is coupled to the nasion pad. The nose contact can have a channel adapted to receive a leg extending from the lens. The lens is coupled to a retractor which provides a force to pull the lens toward the user's face. The eyewear system can be coupled to a helmet or hard hat. The lens is moveable between a first position on the user's face and a second position on the hard hat. The eyewear can be frameless and the retractor can be coupled to an engagement feature on the lens.

19 Claims, 12 Drawing Sheets

(56) References Cited

U.S. PATENT DOCUMENTS

| | | | |
|---|---|---|---|
| 5,790,228 A * | 8/1998 | Bell, III | G02C 3/003 351/111 |
| RE36,048 E | 1/1999 | Schmolz et al. | |
| 5,898,472 A | 4/1999 | Oshikawa | |
| 5,956,115 A | 9/1999 | Bolle | |
| 6,102,542 A | 8/2000 | Masuda | |
| 6,976,756 B1 | 12/2005 | Chen | |
| 7,140,729 B2 | 11/2006 | Resler et al. | |
| 7,147,321 B2 | 12/2006 | Van Atta | |
| 7,314,278 B2 | 1/2008 | Resler et al. | |
| 7,559,647 B2 | 7/2009 | Curiel | |
| 7,631,967 B1 * | 12/2009 | Huang | G02C 5/12 351/106 |
| 7,665,841 B2 | 2/2010 | Resler et al. | |
| 7,712,895 B2 * | 5/2010 | Wang | G02C 1/04 351/106 |
| 7,798,636 B2 | 9/2010 | De La Renaudiere | |
| 8,029,131 B2 | 10/2011 | Assia | |
| 8,210,676 B1 * | 7/2012 | Hunt | G02C 3/02 2/209.13 |
| 8,523,350 B2 | 9/2013 | Krisik et al. | |
| 9,004,680 B2 | 4/2015 | Havens-Olmstead | |
| 2001/0048504 A1 | 12/2001 | Joo | |
| 2011/0317122 A1 | 12/2011 | Havens-Olmstead | |
| 2012/0050666 A1 * | 3/2012 | Havens-Olmstead | G02C 5/126 351/132 |
| 2013/0042393 A1 | 2/2013 | Duran | |

* cited by examiner

SAFETY GLASSES DEPLOYMENT SYSTEM

BACKGROUND OF THE INVENTION

Traditional eyeglass systems include a frame for holding the lenses with arms extending from the frame. The arms are positioned over the user's ears to secure the frames in place. Frames typically include nose contacts which are designed to rest on the bridge of the nose when the glasses are worn.

However, traditional systems can be uncomfortable for the user when used for prolonged periods. These designs also allow the frames some degree of movement as the user performs facial movements such as scrunching their nose. Further, such systems are not designed to prevent rotation of the frames when in use. When the glasses are used for safety, such movement of the glasses can create an unsafe or hazardous situation. For example, rotational and/or upward and downward movement of safety glasses can expose the eyes to external elements, which could all but defeat the purpose of the safety glasses. Therefore, a need exists for an improved system for securing eyewear to a user's face, particularly in situations where a user's safety is the utmost reason for using the eyewear.

BRIEF SUMMARY OF THE INVENTION

One aspect of the disclosure describes eyewear having a lens with a leg extending therefrom and a nasion pad supporting the lens. The nasion pad may have a saddle shape directed toward the user's face and be configured to prevent movement and/or rotation of the eyewear with respect to the user's face. The saddle shape may have a first curve along a first axis and a second curve along a second axis transverse to the first axis. The saddle shape may thus create a single point of contact on the user's face at the nasion. The nasion pad can be coupled to a nose grip which is adapted to receive the leg. The nasion pad and nose grip can alternatively be monolithic. The eyewear can include a nub extending from the lens and an orifice in the nasion pad adapted to receive the nub, which can secure the nasion pad to the lens.

The eyewear can include a retractor coupled to the lens which is adapted to provide a rearward force on the lens with respect to the user's face. The nasion pad may have a convex cross-section along a first axis and a concave cross-section along a second axis. The first axis can extend from the top to the bottom of the nasion pad and the second axis may be perpendicular to the first axis.

The eyewear may be coupled to a hard hat by the retractor. The retractor can include a tether coupled to the eyewear at one end and to a biasing element at the other end, which is then coupled to the hard hat. In one embodiment, the nasion pad can be adapted to provide a frictional force to secure the eyewear in place on the hard hat when the eyewear is removed from the user's face and placed in contact with the hard hat. In one alternative embodiment, the lens may comprise first and second lens members coupled to each other by the nasion pad. Preferably, the eyewear may be safety glasses.

The lens can be moveable between a first position on the user's face and a second position on the hard hat. The nasion pad can be positioned superior to the user's interpupillary line. The eyewear may be frameless and the nasion pad and retractor can each be coupled directly to the lens. A retractor can have a housing coupled to a hard hat liner, a biasing element within the housing, and at least one tether coupled to the lens such that the biasing element provides a rearward force on the lens with respect to the user's face.

DETAILED DESCRIPTION

Figure 1:
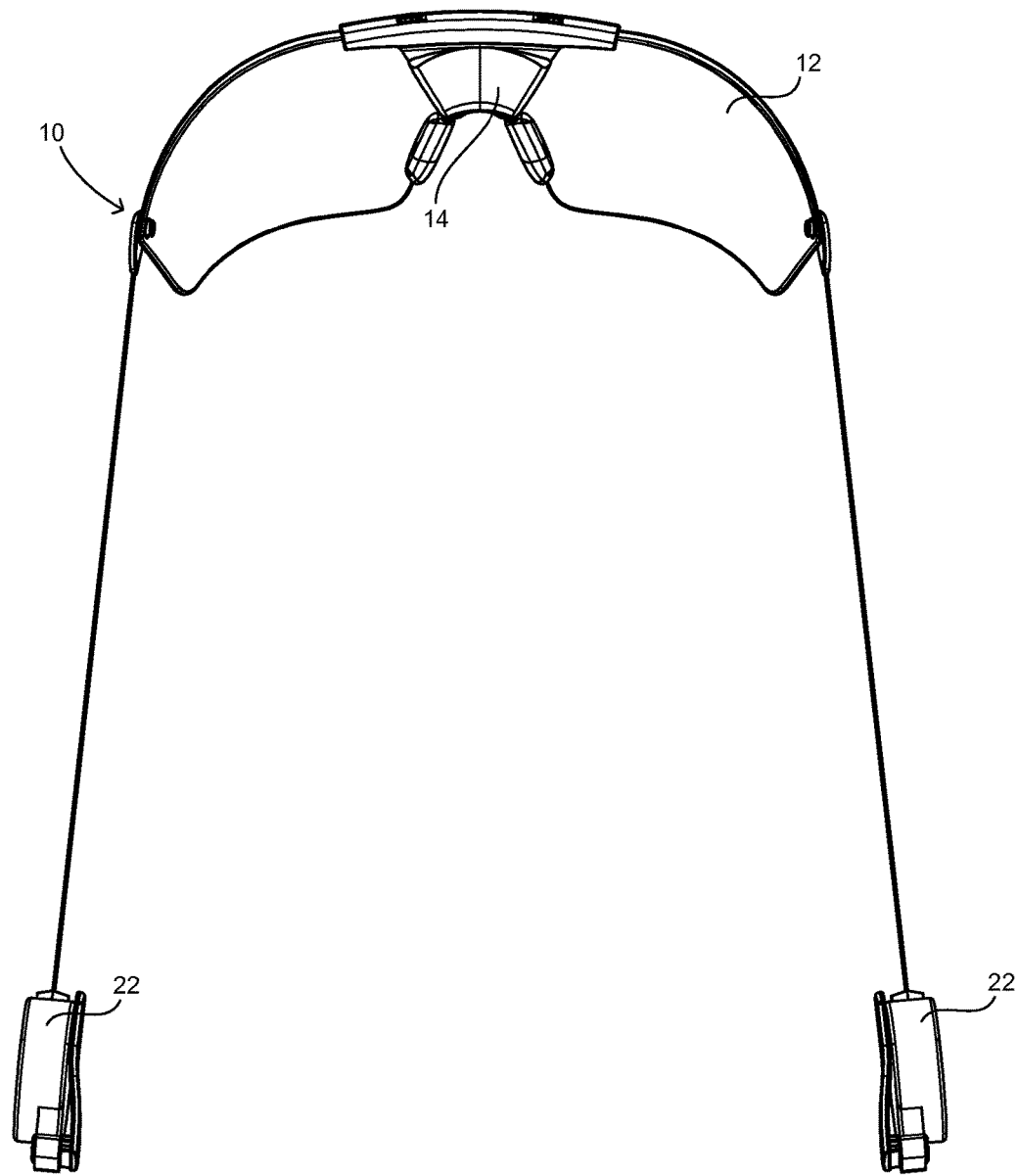
FIG. 1 illustrates a perspective view of an eyewear system in accordance with one embodiment of the present invention.
Figure 2:
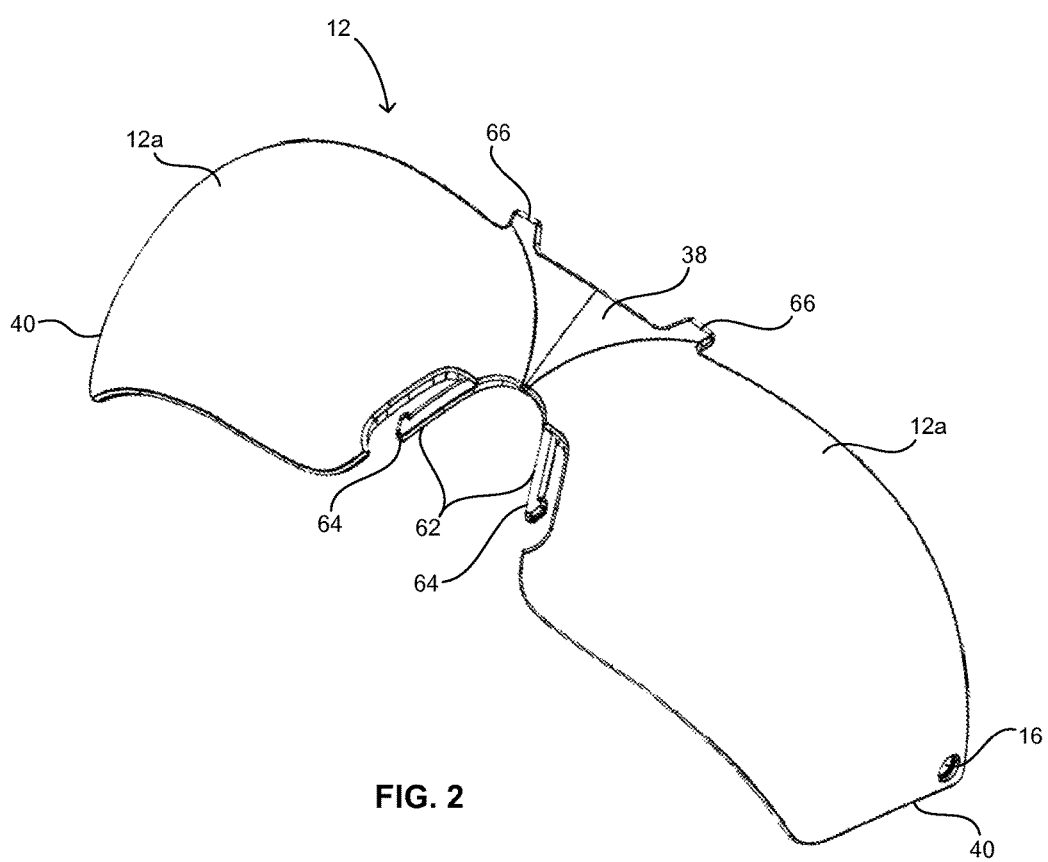
FIG. 2 illustrates a perspective rear view of the lens of FIG. 1.
Figure 3:
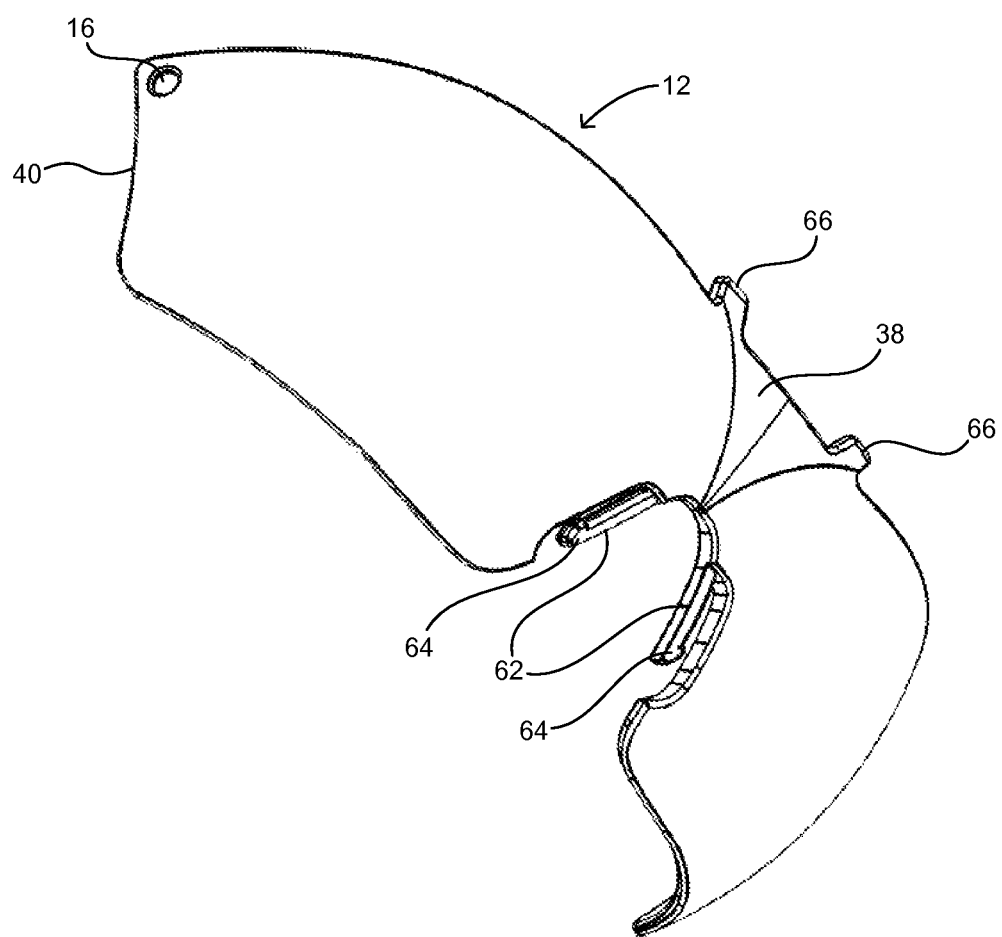
FIG. 3 illustrates a front perspective view of the lens of FIG. 1.

One embodiment of an eyewear system is shown in FIG. 1. The eyewear 10 in this embodiment is frameless and includes a lens 12 which can be used to protect a user's eyes from debris, glare, wind, extreme temperatures, etc. The lens could also be a prescription lens to enhance a user's vision. One lens contemplated for use with the current system is that which is employed in the Foresigh™ Safety Glasses manufactured by Worldwide Vision Tech. (Oak Ridge, N.J.). The lens 12 shown in FIGS. 1-3 is depicted as a monolithic construct having lenses 12*a* joined by a connector 38. Alternatively, the lens could simply be a continuous piece of lens material such that connector 38 is not required. Further, separately formed lenses connected by a nasion pad (discussed below) are also contemplated. The lens can preferably be constructed of polycarbonate or similar material which provides a scratch resistant surface.

While the embodiments discussed herein pertain to safety glasses, which may be used with hard hats, it should be appreciated that the eyewear system disclosed herein may be used with other lens and in other applications, such as ski goggles (with or without a helmet), motorcycle and bicycle glasses or goggles (with or without a helmet), and the like.

Continuing with the embodiment of eyewear 10, legs 62 are shown extending from the connector 38 in FIGS. 2-3. Each leg has a foot 64 extending from the free end of the leg. The legs 62 couple the lens 12 to a nasion pad as explained below. Nubs 66 are formed at the top of the connector 38 which also assist in securing the nasion pad to the lens.

The lens 12 includes an engagement feature 16 to couple to a retractor 22. The engagement feature 16 of FIG. 2 is a through hole in a lateral portion 40 of the lens 12. The engagement feature 16 could alternatively be glue, Velcro, a weld, a fastener, etc. In some embodiments, the engagement feature and retractor provide a detachable connection with the lens to allow one of the lens and retractor to be replaced as desired without discarding the other. Providing such detachment also may allow for ease of cleaning the lens. As described further below, it is believed that having an engagement feature on the lateral portion of the lens assists in maintaining the position of the lens on the center of the user's face while avoiding or reducing any interference with a user's vision.

Figure 4:
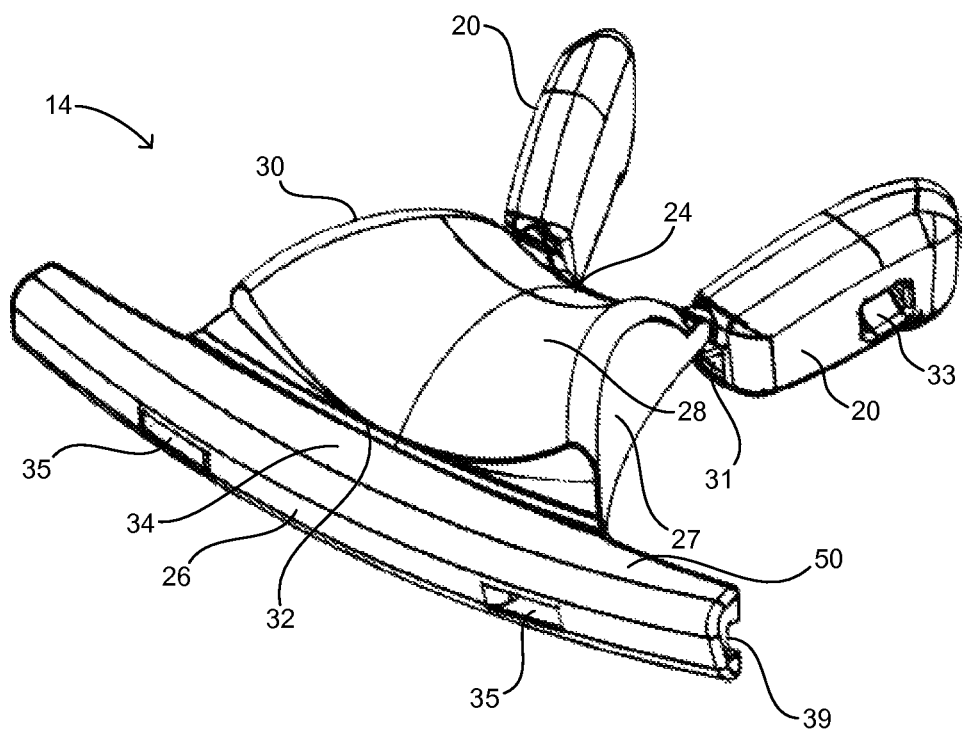
FIG. 4 illustrates a front perspective view of the nasion pad of FIG. 1.
Figure 5:
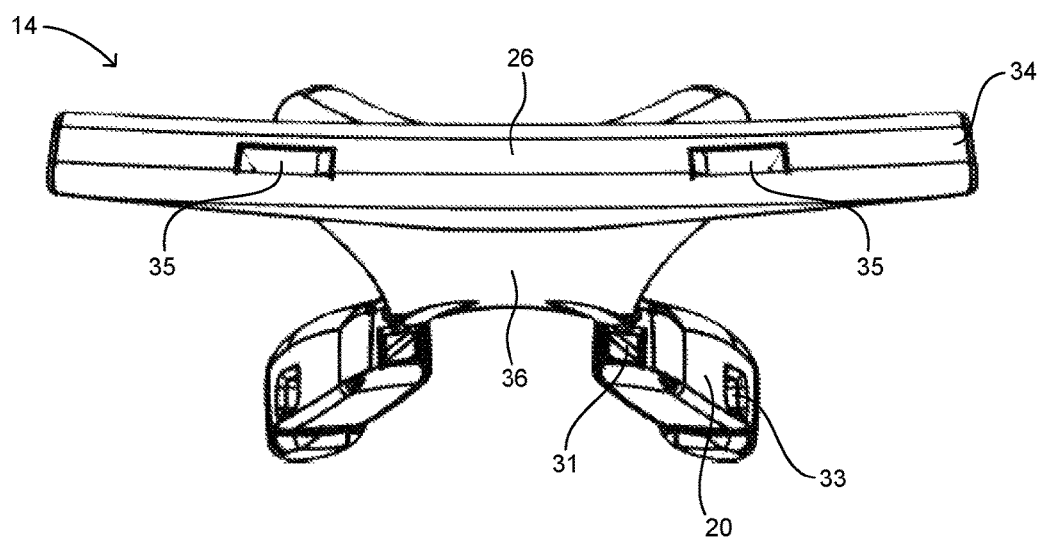
FIG. 5 illustrates a top perspective of the nasion pad of FIG. 1.
Figure 6:
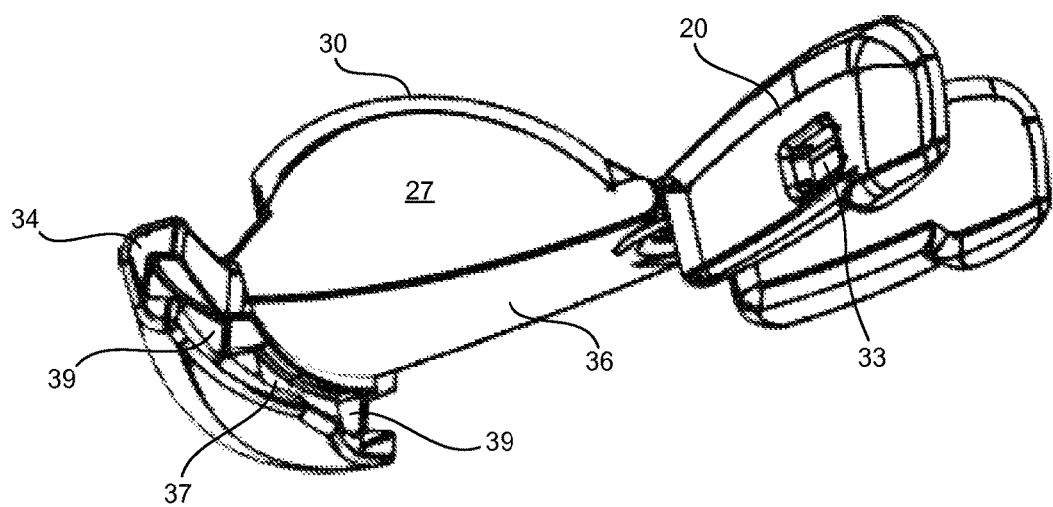
FIG. 6 illustrates a side perspective view of the nasion pad of FIG. 1.
Figure 10:
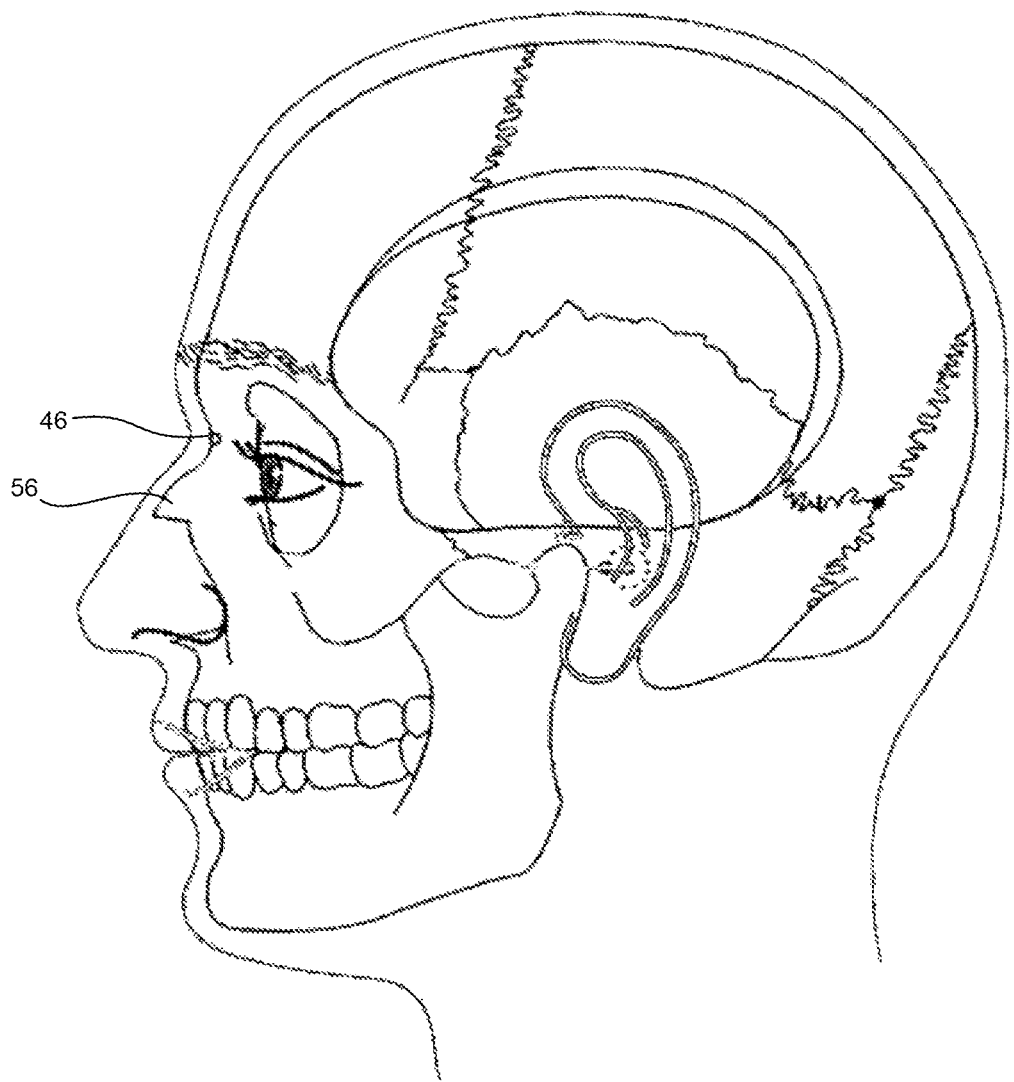
FIG. 10 illustrates a profile of a user's face.

FIGS. 4-6 illustrate one embodiment of a nasion pad having a saddle 28 sized and shaped to fit within the nasion of a user. The nasion 46 is the depressed area superior to the bridge 56 of the nose as best seen in FIG. 10. The nasion 46 is formed at the intersection of the bones of the forehead and the nose. The saddle 28 has a convex first curve 30 along a first axis extending between the upper end 26 and the lower end 24 of the nasion pad 14. The saddle 28 also has a concave second curve 32 extending laterally across the saddle along a second axis transverse to the first axis. The saddle 28 is directed toward the user's face when the nasion pad 14 is coupled to the lens 12 and the eyewear system 10 is in use, such that the curves of the saddle 28 are shaped to properly fit within the anatomy of the nasion 46. For instance, the concave second curve 32 may be designed to straddle the convex shape of the nasion, from side to side, which exists due to the intersection of the nose bone at the nasion. The concave shape may help to further secure the eyewear in place and minimize relative motion of the eyewear to the face. For example, the saddle shape may help prevent yaw and pitch rotation of the eyewear with respect to the user's face.

Extension elements 20 are coupled to the lower end 24 of the nasion pad 14 in FIGS. 4-6. In other embodiments, if present at all, the nose contacts or extension elements 20 are formed separately from the nasion pad 14 and are connectable with the nasion pad 14, or alternatively, may remain separate from the nasion pad and instead simply engage to the lens independent of the nasion pad. The extension elements 20 may engage legs 20 in any way desired, which may provide further stability of the connection between the nasion pad and the lens. For example, in this embodiment, a channel may be formed in each extension elements 20 to receive a leg 62 of the lens 12. The channel tunnels between a first opening 31 and a second opening 33. Once inserted, the leg 62 extends through the first opening 31 toward the second opening 33. In some embodiments, the foot 64 can extend out of the second opening 33 to prevent dislodgement of the nasion pad 14 from the lens 12. A portion of the extension element 20 occupies at least some of the space between the leg 62 and the lens 12. The extension element 20 should be shaped such that any contact with the user's nose will be comfortable to the user, though constant contact and/or support of the nose contact on the nose of the user is not intended or necessary. In other words, the extension elements can provide support for the lens which is ancillary to the primary stabilization provided by the nasion pad and retractor.

Further stability of the connection between the nasion pad 14 and the lens 12 may be achieved other than on the legs 62 and extension element 20. For example, the nasion pad 14 may include a tab 34 formed at the upper end 26 of the nasion pad 14 as shown in FIGS. 4-6. The tab may be of any shape suitable to engage the nasion pad with the lens. For example, the tab 34, as illustrated, may extend above the rear surface 36 and/or saddle 28 of the nasion pad to secure to the top of the lens and connector (if present). As illustrated, the tab 34 extends rearwards to have a U-shape, forming grooves 37, 39, to extend over the lens 12 and engage the nubs 66. Orifices 35 may be formed in the tab 34 and are designed to receive the nubs 66 of the lens 12, as in FIG. 2. The tab 34 has a front surface 50 which can be shaped to minimize and/or avoid contact with the user's forehead when the eyewear system is in use. A medial groove 37 and a lateral groove 39 may be formed on the underside of the tab 34 (best seen in FIG. 6), based on the U-shape of tab 34. The medial groove 37 may be adapted to receive the portion of the connector 38 between the nubs 66 (if connector is not present, medial groove 37 may engage the upper portion of the lens 12). The lateral groove 39 may be adapted to receive the upper portion of the lens 12. The lateral groove 39 and medial groove 37 may have a similar shape and be separated by the orifice 35. In other embodiments, the grooves may be of different shapes to accommodate a lens where the upper ends of the lens and connector are not coplanar, have different thicknesses, etc. The tab 34 as shown in FIGS. 4-6 extends laterally beyond body 27 of the nasion pad 14. The tab could also extend laterally the entire length of the lens or, alternatively, not extend past the body.

Figure 11:
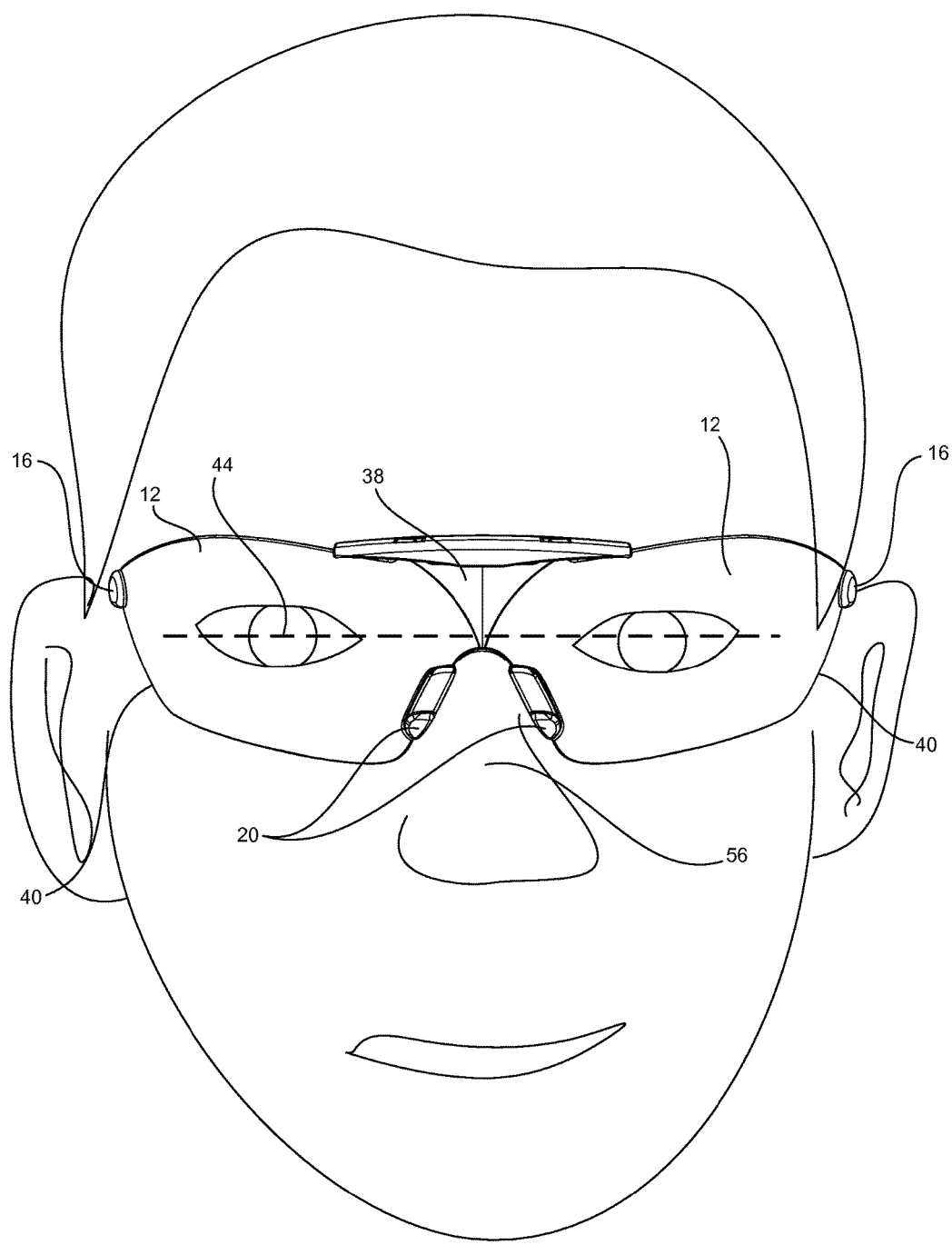
FIG. 11 illustrates the eyewear system of FIG. 1 on a user's face.

Preferably, the nasion pad 14 provides the primary stabilizing force for the eyewear system with regard to the user's face. As shown in FIG. 11, the nasion pad 14 is configured to be positioned superior to the user's interpupillary line 44 when the eyewear system is in use. In other words, the saddle 28 contacting the nasion 46 is the only contact between the nasion pad 14 and the user's face. This is particularly beneficial because the nasion 46 is one of the few areas of the face, if not the only area, that does not move, or does not significantly move, when a person makes facial expressions. In contrast, the nose and forehead both have movements in most facial expressions, and in certain facial expressions (e.g., scrunching the nose, furrowing the brow, etc.), the movement of the nose and/or forehead can be drastic. As such, the present invention, focusing on the nasion for contact of the eyewear system to the face, results in a more stable eyewear system for the user that may not move (and certainly, at worst, has only minimal movement) with the user's facial expressions. For example, the extension elements provide ancillary stability of the eyewear system and are adapted to allow movement of the nose with respect to the extension elements such that scrunching of the nose will not cause movement, or at least significant movement, of the lens with respect to the user's face because the system is anchored by the nasion pad. Therefore, in the particular example of the eyewear system 10 being safety glasses, the stability of the lens on the user's face may increase the safety and effectiveness of the eyewear system, in addition to being more comfortable for the user and providing less irritation and aggravation to the user.

Figure 7:
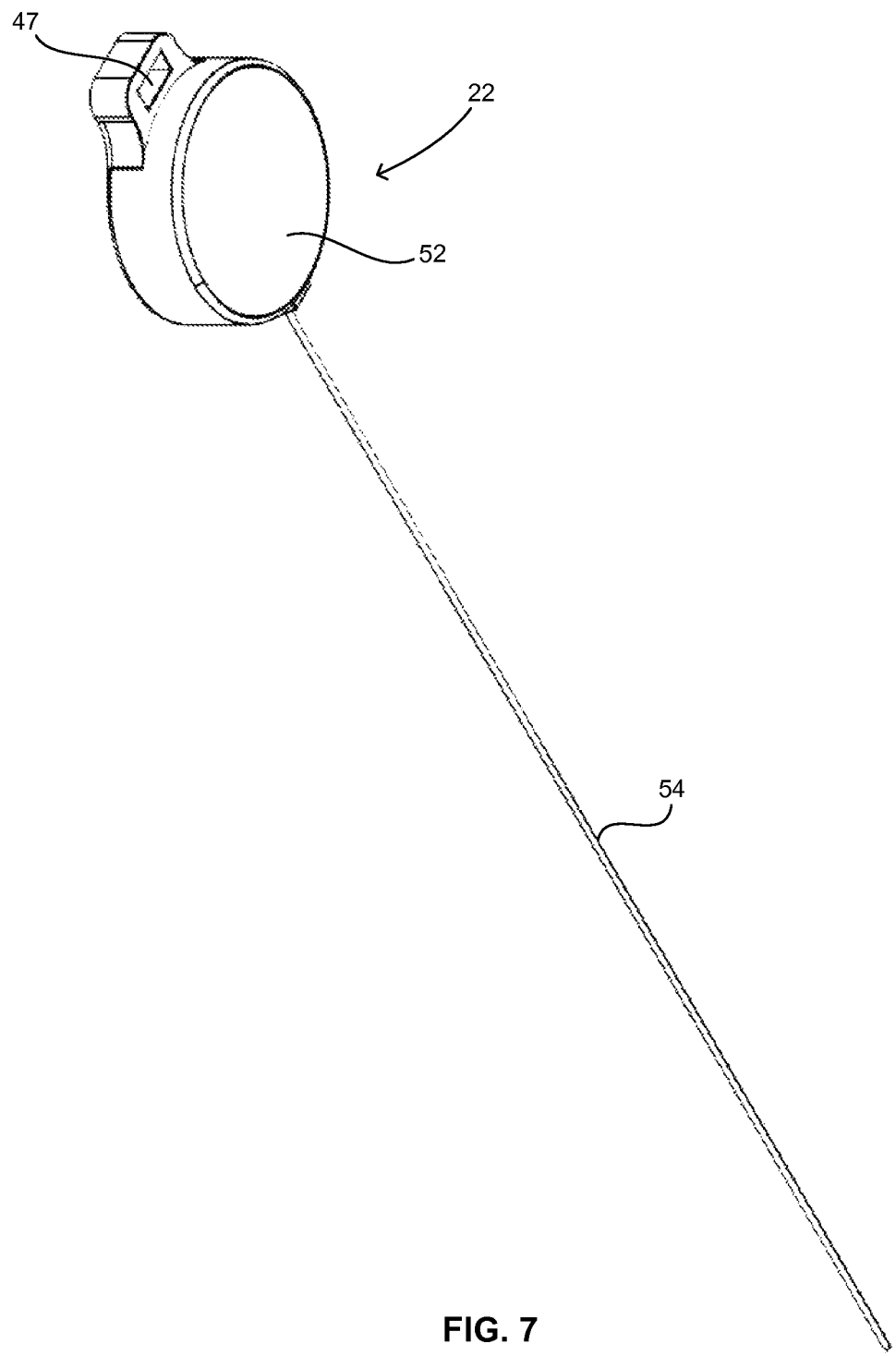
FIG. 7 illustrates the retractor of FIG. 1.

Returning to the embodiment of the eyewear system 10 of FIG. 1, the system also includes retractors 22 which bias the lens 12 toward the user's face. The retractor 22 shown in FIG. 7 includes a tether 54 extending from a housing 52. The tether is preferably a flexible member which is coupled to the engagement feature 16 of the lens 12 by a holder 49. The housing 52 contains a biasing element (not shown) which provides a retraction force on the tether. One type of retractor contemplated for use with the current system is described in U.S. Pat. No. 6,929,209, the disclosure of which is hereby incorporated by reference herein. In other embodiments, the tether 54 can be a stretchable member adapted to provide a retracting force to supplement or replace the biasing element in the housing.

Figure 9:
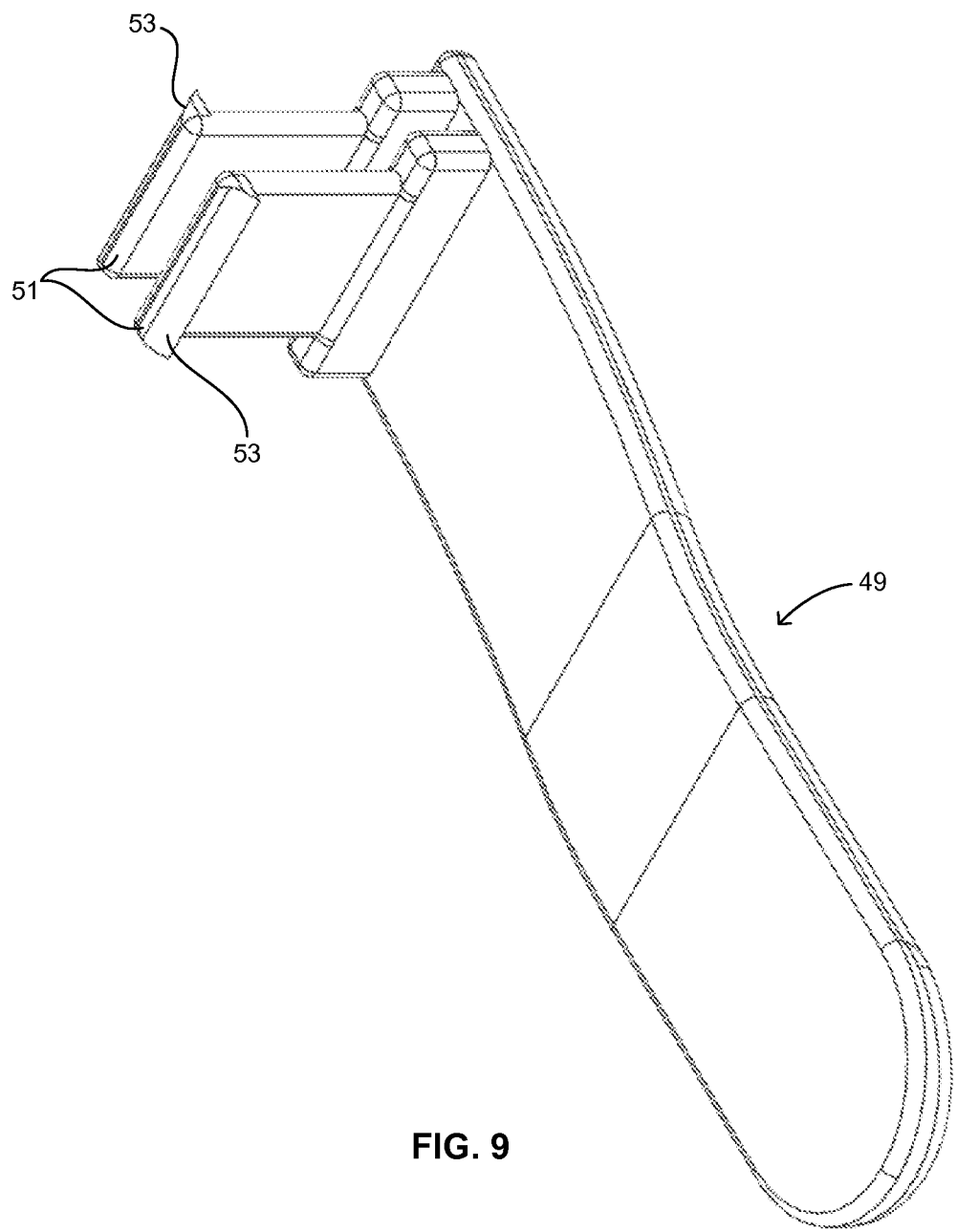
FIG. 9 illustrates the attachment element of FIG. 1.

The housing may include a structure for securing the retractors 22 to a stationary structure relative to the lens 12, such as a hard hat. For example, a receiver 47 (FIG. 7) can accept a holder 49 (FIG. 9), where the holder is attached to the hard hat, for example. The holder 49 shown in FIG. 9 has teeth 53 extending from arms 51. The arms 51 can be inserted through the receiver 47 allowing the teeth 53 to emerge from the opposite side of the receiver 47 where the teeth create an interference fit with the receiver, thus securing the holder 49 to the housing 52. Alternatively, the system 10 may include only a single retractor which may be positioned behind the user's head to attach to both ends of the lens 12.

Figure 8:
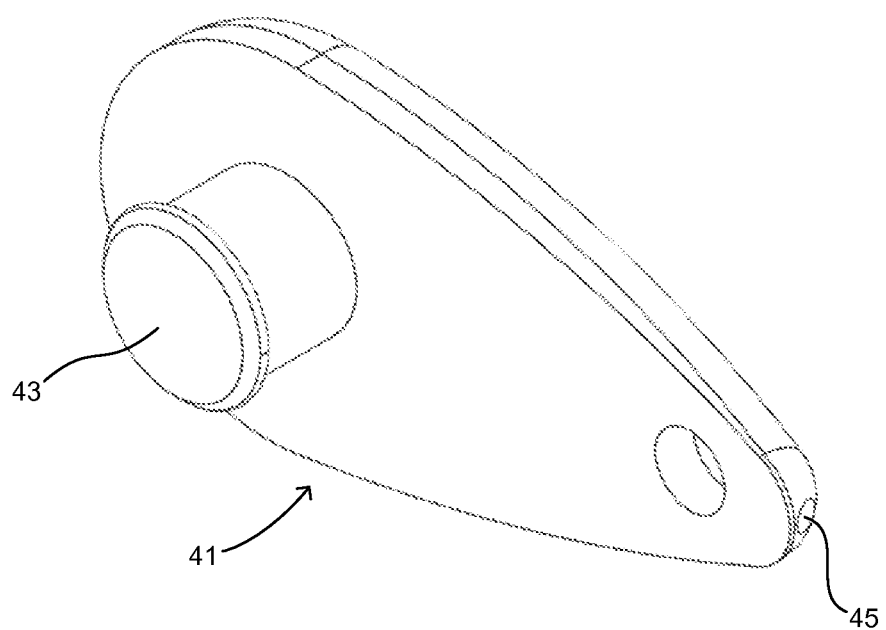
FIG. 8 illustrates the lens clip of FIG. 1.

The tether 54 is connected at the other end directly to the lens 12 or to an intermediate structure, such as an attachment element 45 of a lens clip 41. The lens clip 41 shown in FIG. 8 includes a stud 43 which is adapted to engage the engagement feature 16 on the lens 12.

In one instance, the retractor allows the lens to be transitioned between a position on the user's face and a position away from the user's face. For example, when the eyewear system is coupled to a helmet (for example, a hard hat) as described below, the user can move the eyewear off of their face and place it in stationary contact with the helmet. The retractor provides a rearward force on the lens to maintain the position of the eyewear on the helmet. The nasion pad can be manufactured of a material (e.g. rubber, foam, silicon, PVC, polycarbonate, shape memory polymer) that provides a frictional force when placed in contact with the helmet to further maintain the position of the eyewear on the helmet. In other embodiments, the eyewear system can include a sleeve attached to the helmet which receives the eyewear when not in use as explained below with regard to FIG. 12.

When in use on a user's face, the amount of force provided by the retractor can be such that the friction created between the nasion pad and the user's nasion provides the primary stabilizing force is sufficient to hold the lens in place. Further, the upper portion of the nose, meeting the forehead at the nasion, may also provide a sufficient "stop" such that, when coupled with the rearward force supplied by the retractors 22, partially or completely overcomes gravity and thereby maintains the position of the lens on the user's face. In other words, unlike previous eyewear systems, the present system does not rely on gravity to maintain the position of the lens on the user's face. As such, the retractor combined with the shape of the nasion pad stabilizes the lens on the user's face whether the user is upside down, sideways, etc. By this combination of the shape of the saddle 28 of the nasion pad with the rearward tension from the retractors, the nasion pad can be the only element of the eyewear system that contacts the user's face.

The retractor housing can be coupled by the holder 49 to a helmet (e.g. firefighter, bicycle, motorcycle, construction helmet). Some helmets include a liner such as that described in U.S. Pat. No. 3,633,214, the disclosure of which is hereby incorporated by reference herein. The retractor 22 can be removably coupled to the suspension device or liner by the attachment element 45. Of course, the retractor could also be permanently attached or formed monolithically with the liner. The retractor could also be coupled to a brim of the helmet by a feature such as that disclosed in U.S. Pat. No. 6,892,393, the disclosure of which is hereby incorporated by reference herein. It is believed that incorporating two retractors coupled to the liner on opposing sides of the helmet assists in maintaining the position of the eyewear in the center of the user's face.

Figure 12:
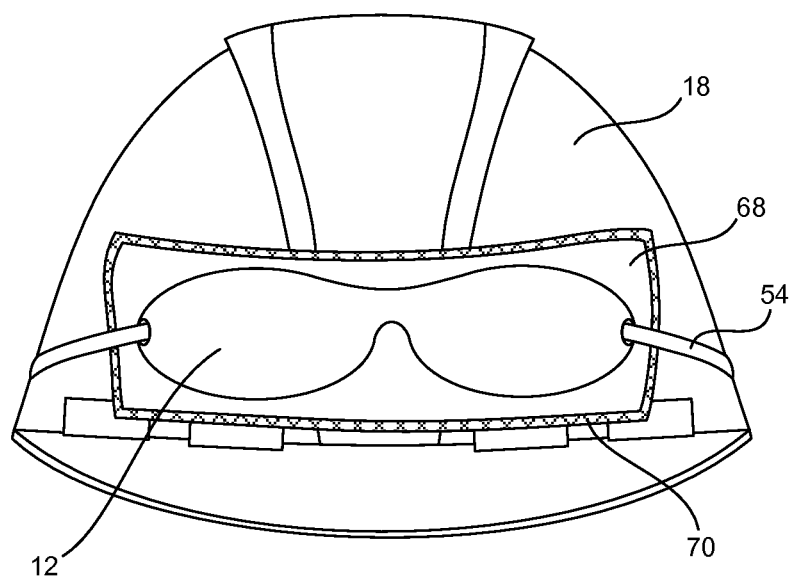
FIG. 12 illustrates the eyewear system of FIG. 1 coupled to a hard hat.

An eyewear system can also optionally include a pouch 68 or holder to receive the lens 12 when not in use as shown in FIG. 12. The pouch 68 is shown coupled to the front of a hard hat 18. Of course, the pouch could also be positioned on the side, back, or top of the hard hat. The pouch 68 is preferably made from microfiber cloth, plastic, or similar material to protect the lens from debris, oil, etc. which could scratch or otherwise impair use of the lens 12. The pouch 68 can be coupled to the hard hat 18 by a temporary connection (e.g. Velcro) or a permanent connection (e.g. adhesive). The pouch can be sealed on one or more sides such that the lens is slipped into the pouch. In other embodiments, the pouch can be a single element that folds over the lens once the lens is in place and is secured with a button or Velcro. Preferably, as illustrated in FIG. 11, the pouch is positioned in a location where the user can raise the lens from their face and onto the hard hat, such that the tether 54 can remain attached to the lens and assist in keeping the lens in position at or in the pouch.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An eyewear comprising:
    a lens;
    a leg extending from the lens;
    a nasion pad supporting the lens and having a saddle shape directed toward a user's face and configured to prevent at least one of movement and rotation of the eyewear with respect to the user's face, the saddle shape having a convex cross-section along a first axis, a concave cross-section along a second axis transverse to the first axis, and a single point of contact on the user's face at the nasion; and
    a nose contact coupled to the nasion pad having a channel adapted to receive the leg.

2. The eyewear of claim 1, further comprising a retractor coupled to the lens, the retractor including a biasing element adapted to provide a rearward force on the lens with respect to the user's face.

3. The eyewear of claim 1, further comprising:
    a nub extending from the lens; and
    an orifice in the nasion pad adapted to receive the nub.

4. The eyewear of claim 3, further comprising a tab coupled to an upper portion of the nasion pad, the tab extending laterally beyond a body of the nasion pad;
    wherein the nub and the orifice are formed on the tab.

5. The eyewear of claim 1, wherein the nasion pad and the nose contact are monolithic.

6. The eyewear of claim 1, wherein the eyewear comprises safety glasses.

7. The eyewear of claim 1, wherein the first axis extends from the top to the bottom of the nasion pad and the second axis extends perpendicularly to the first axis.

8. An eyewear system comprising:
    a lens coupled to a hard hat, the lens moveable between a first position on a user's face and a second position on the hard hat;
    a nasion pad shaped to fit against the user's nasion to position the eyewear on the user's face, the nasion pad located superior of the user's interpupillary line, and the naison pad having a first curve along a first axis and a second curve along a second axis transverse to the first axis; and
    a retractor having a first end coupled to the lens and a second end coupled to the hard hat, the retractor including a biasing element configured to provide a rearward force on the lens with respect to the user's face.

9. The eyewear system of claim 8, wherein the eyewear is frameless and the nasion pad and retractor are each directly coupled to the lens.

10. The eyewear system of claim 9, further comprising a nose contact coupled to the lens.

11. The eyewear system of claim 8, wherein the lens comprises first and second lens members coupled to each other by the nasion pad.

12. The eyewear system of claim 8, wherein the retractor is adapted to be coupled to a liner within the hard hat.

13. The eyewear system of claim 8, wherein the retractor is coupled to an engagement feature in the lens.

14. The eyewear system of claim 8, wherein the retractor comprises a housing, a biasing element within the housing, and a tether having a first end coupled to the biasing element and a second end coupled to the lens.

15. The eyewear of claim 8, wherein the first axis extends from the top to the bottom of the nasion pad and the second axis extends perpendicularly to the first axis.

16. The eyewear of claim 8, wherein the nasion pad is adapted to provide a frictional force to secure the eyewear in place on the hard hat when the eyewear is removed from the user's face and placed in contact with the hard hat.

17. The eyewear of claim 8, wherein the retractor is removably coupled to the hard hat.

18. A frameless eyewear system comprising:
a lens having an engagement feature coupled to a hard hat;
a leg extending from the lens;
a nasion pad having a saddle shape configured to fit against a user's nasion to position the eyewear on the user's face, the nasion pad having a first curve along a first axis and a second curve along a second axis transverse to the first axis;
a nose contact coupled to the nasion pad having a channel configured to receive the leg; and
a retractor coupled to the hard hat and the engagement feature, the retractor configured to provide a rearward force on the lens with respect to user's face;
wherein the frameless eyewear is moveable between at least a first position on the user's face and a second position on the hard hat.

19. The frameless eyewear system of claim 18, wherein the saddle shape of the nasion pad is directed toward the user's eyes and is configured to prevent lateral and longitudinal movement of the frameless eyewear with respect to the user's nose and/or forehead and the nasion pad is configured to prevent yaw and pitch rotation of the frameless eyewear with respect to the user's face.

* * * * *